United States Patent [19]

Pullan

[11] Patent Number: 5,099,129

[45] Date of Patent: Mar. 24, 1992

[54] MULTIPLE SAMPLE RADIOACTIVITY DETECTOR

[76] Inventor: Brian R. Pullan, 167 Bramhall Lane South, Bramhall, Stockport, England, SK7 2NG

[21] Appl. No.: 18,671

[22] PCT Filed: Nov. 20, 1985

[86] PCT No.: PCT/GB85/00532

§ 371 Date: Sep. 18, 1986

§ 102(e) Date: Sep. 18, 1986

[87] PCT Pub. No.: WO86/03332

PCT Pub. Date: Jun. 5, 1986

[51] Int. Cl.⁵ .............................................. G01T 1/185
[52] U.S. Cl. .................................. 250/385.1; 250/374; 250/375
[58] Field of Search ..................... 250/374, 375, 385.1

[56] References Cited

U.S. PATENT DOCUMENTS 3,418,474 12/1968 Spergel et al. ................... 250/385.1
3,911,279 10/1975 Gilland et al. ................... 250/385.1
4,639,601 1/1987 Pullan ............................... 250/385.1

FOREIGN PATENT DOCUMENTS 2190787 11/1987 United Kingdom ............. 250/385.1

Primary Examiner—Carolyn E. Fields
Assistant Examiner—Drew A. Dunn
Attorney, Agent, or Firm—Michael Ebert

[57] ABSTRACT

A detecting system capable of simultaneously detecting radioactive emissions from a multiplicity of samples uses a sample holder containing a multiplicity of receiving zones and a multiplicity of drift chambers corresponding respectively to each receiving zone and also having one or more apertures. An array of cathodes is disposed transversely to an array of anodes and the crossing points corresponds to the apertures. There is also a structure that eliminates cross talk between the chambers. This structure is arranged so that a potential difference can be applied across the sample holder which in turn creates a field within the drift chambers in order to improve the detection gain of the detector head assembly.

11 Claims, 4 Drawing Sheets

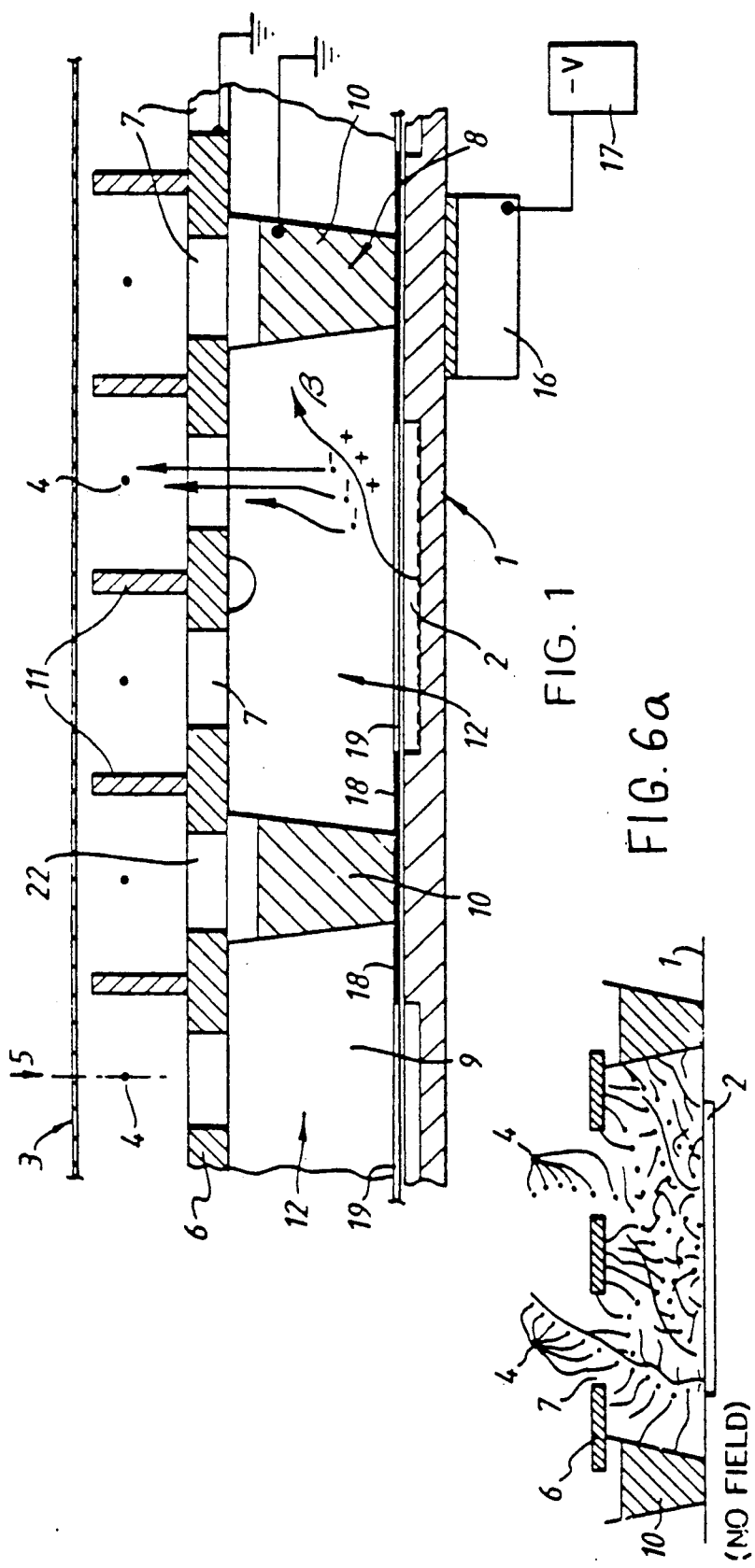
FIG. 1
FIG. 6a (NO FIELD)
FIG. 6b (FIELD APPLIED)

MULTIPLE SAMPLE RADIOACTIVITY DETECTOR

BACKGROUND OF INVENTION

1. Field of Invention

This invention relates to a detecting head assembly capable of simultaneously detecting radioactive emissions (such as beta particles) from a multiplicity of samples. The detecting head assembly may be used in apparatus for counting ionizing events due to beta particles emitted by a radiochromatogram or an electrophoretogram (hereinafter called "radiograms"), or by biological or other samples.

2. Status of Prior Art

A detecting head assembly is already known from EP-A-0112645 which comprises electrode sub-assemblies including a grid of cathode strips which cross over an array of anode wires to form a plurality of detector crossing points. The crossing points detect individual ionizing events due to the ionization of a gas or mixture of gases by beta particles emitted from radioactive materials in a radiogram. In order to improve spatial resolution, a mask having a plurality of radiation transmissive zones or apertures (corresponding in position and number with the anode/cathode crossing points) is supported between a sample holder and the electrode sub-assemblies. The detecting electrode sub-assemblies and the mask are mounted in scanning means which are slidably supported in juxtaposition to the sample holder. The detecting electrode sub-assemblies (crossing points) can thereby be scanned across a sample. In a preferred arrangement, respective 'x' and 'y' coordinate stepper motors are used to provide a raster scan of a plurality of regions or frames in the sample zone. The output signals from the detecting electrode assemblies are supplied to either conventional pulse counting means, or they are coded (with respect to the position coordinates of individual ionization events) and the coded signals are then supplied to a computer where they are processed in order to derive information relating to the distribution of radioactivity in the sample.

The apparatus described in EP-A-112645 is particularly useful in providing a high resolution "picture" of the spatial distribution of radioactivity in a radiogram and it was primarily developed for visualising the distribution of radioactivity in a sample. There is, however, a need for an efficient, multiple sample, radioactivity detector of relatively straightforward and robust construction which can be used, for example, in the field of medical diagnostics and biomedical research, to count beta particle emissions from radioactive materials taken from radiograms or in biological or other samples where only the radioactivity of the samples is required and not the distribution of radioactivity within a sample. The present invention seeks to solve this problem.

SUMMARY OF INVENTION

The main object of this invention is to provide a detector head assembly capable of detecting radioactive emissions such as beta particles from multiplicity of samples.

Briefly stated, this object is attained in detector head assembly comprising:

(a) a sample holder which defines a multiplicity of sample receiving zones;

(b) structure defining multiplicity of drift chambers corresponding respectively with said sample receiving zones, the structure defining each of said drift chambers having one or more apertures for passage therethrough of ions resulting from ionization of gas within said chambers due to radioactive emission;

(c) detecting electrode means including an array of anodes which are disposed transversely of an array of cathodes so as to define a plurality of crossing points, said crossing points being disposed so as to correspond with the respective apertures in said structure; and (d) means for isolating neighbouring regions in the vicinity of said crossing points so as to reduce, or substantially eliminate mutual interference between adjacent crossing points;

the arrangement being such that potential difference can be applied across the sample holder and said structure to create a field within each of said drift chambers, which field causes said ions to pass through said apertures for detection by the respective crossing points, said field being applied to improve the detection gain of the detector head assembly.

Preferably, the structure defining each of the drift chambers has a plurality of apertures therein (each with its associated detector crossing point, since this increases the sample area for detecting radioactive emissions. This is advantageous in that thin samples are best for reducing self absorption to a minimum (and hence a larger volume of sample can be included in a larger sample area). However, only one aperture may be provided in the structure for each drift chamber where, for example, vary small samples are to be used and the associated sample holder has a corresponding multiplicity of shallow wells. These wells may contain, for example, respective thin dried samples derived from liquid samples taken by syringe. Clearly, the number of apertures which are used in practice will depend on particular usage or requirements. Incidently, where the samples are radiograms, they may be portions which are cut out from a larger sample, the portions being those which contain radioactivity to be detected. Clearly, information relating to such portions can be related to a larger sample from which they were removed.

The structure defining the drift chambers may include respective apertured plates, a first plate containing the apertures and a second plate defining walls which extend between the first plate and the sample holder. Whilst the plates may be of integral construction, they are preferably separate. The first plate or mask may be constructed as described in EP-A-0112645. Suitably, the second plate is of integrally moulded form, for example it can be made of an electrically conductive material which is easy to cast into a required shape (casting metal such as a tin-lead alloy is suitable for this purpose). One advantage of this is that where the structure has been specially designed for a particular purpose, or to suit a particular customer's requirements, it can be readily moulded and fitted to a basic assembly. In a preferred embodiment of the invention, the second plate has a multiplicity of rectangular apertures therein, the material of the plate defining the side walls of a multiplicity of rectangular drift chambers. Where a gas, or a mixture of gases, are used to purge the drift chambers to enable efficient collection of ions, the second plate (e.g. the rectangular side walls) may contain openings to allow intercommunication between adjacent drift chambers to allow the gas or gases to permeate throughout the structure.

Suitably, the detecting electrode means is of the form described in EP-A-0112645, i.e. wherein an array of anode wires cross a grid of cathode strips. Preferably, the anode wires are located in respective channels extending across that part of the structure defining the apertures (but without obscuring the same). The channels thereby provide means for isolating neighbouring regions in the vicinity of the crossing points so as to reduce, or to substantially eliminate mutual interference or "crosstalk" between adjacent crossing points. In a preferred arrangement, the channels are defined by electrically conductive confronting walls extending across and in electrical contact with a conductive plate containing the apertures, a space above each wall enabling the flow of gas for promoting ionization.

The sample holder is preferably made of electrically conductive material and slidably received (like a drawer) within the detector head assembly. In this case, a sheet or layer of insulation is interposed between the electrically conductive structure which defines the drift chambers and the sample holder. In the preferred embodiment of the invention, which is used for detecting beta particles, a negative potential sources is connected to the sample holder and the structure defining the drift chambers and the isolating means is earthed or grounded. The negative potential source may be variable to provide the required effect.

In a further embodiment of the invention, the structure defining the drift chambers, e.g. the second plate which defines the side walls, is connected to a source of variable potential whilst a (variable) negative potential source is connected to the sample holder. This enables the potential on the structure to be varied by either a positive or negative amount so as to attain optimum results.

The detecting head assembly of the invention is preferably connected to (conventional) signal processing means, e.g. of the type which employs delay lines, means for measuring time delays for the signals or ionizing events detected by the crossing points and a microprocessor for assigning position coordinates to each signal or event. Conventional means of the latter type are described in a paper by Scott, et all in Analytical Biochemistry, Vol. 123, 1-10 (1982). However, the detecting head assembly may alternatively be connected to the signal processing means described in EP-A-0112645 (which includes means for coding the output signals from the detecting electrodes with regard to position coordinates of individual ionizing events, and a processor for processing the coded signals in order to provide an output related to the distribution of radioactivity).

BRIEF DESCRIPTION OF DRAWINGS

A preferred embodiment of the invention will now be described with reference to the accompanying schematic drawings, in which:

FIG. 1 is a cross sectional elevation through part of a detecting head assembly in accordance with an embodiment of the invention.

FIGS. 6a and 6b are schematic views of a sample and the effects of the electric field on the path of negative ions produced by beta particles passing into the drift chamber space.

Referring to FIGS. 1-4, a detecting head assembly according to a preferred embodiment of the invention essentially comprises a sample holder 1 defining a multiplicity of sample receiving zones 2 in the form of shallow wells; a detecting electrode sub-assembly including an array of cathode strips 3 which cross-over an array of anode wires 4 (to form crossing points 5); structure including an apertured plate of mask 6 with through holes 7 and an apertured plate 8 (see FIGS. 2 and 4) with through holes 9 bounded by walls 10; and means (such as walls defining channels) for isolating anode wires 4 from one another so as to prevent "cross-talk" due to radiation entering an adjacent channel.

The sample holder 1, the mask 6 and the walls 10 together define a multiplicity of drift chambers 12 of generally square cross section. As shown in FIG. 1, a beta particle emitted from a sample passes through a mixture of gases within one of the drift chambers 12, thereby creating negative (−) and positive (+) ions. A potential difference applied between the sample holder 1 and the structure including the apertured plates 6 and 8 creates an electrical field within each of the drift chambers 12 which causes a significant fraction of the negative ions to pass through holes 7 (in mask 6) whereby they are captured by anode wire 4 at the respective anode/cathode crossing point 5. The resulting signal (on the anode wire 4 and cathode strip 3) is processed as a beta particle count at respective position coordinates. The position coordinates are used (as explained below) to associate the beta particle emissions with respective samples in the holder 1 when the signals are processed, e.g. by a computer.

The structure and operation of the detector head assembly will now be described in more detail.

Figure 2:
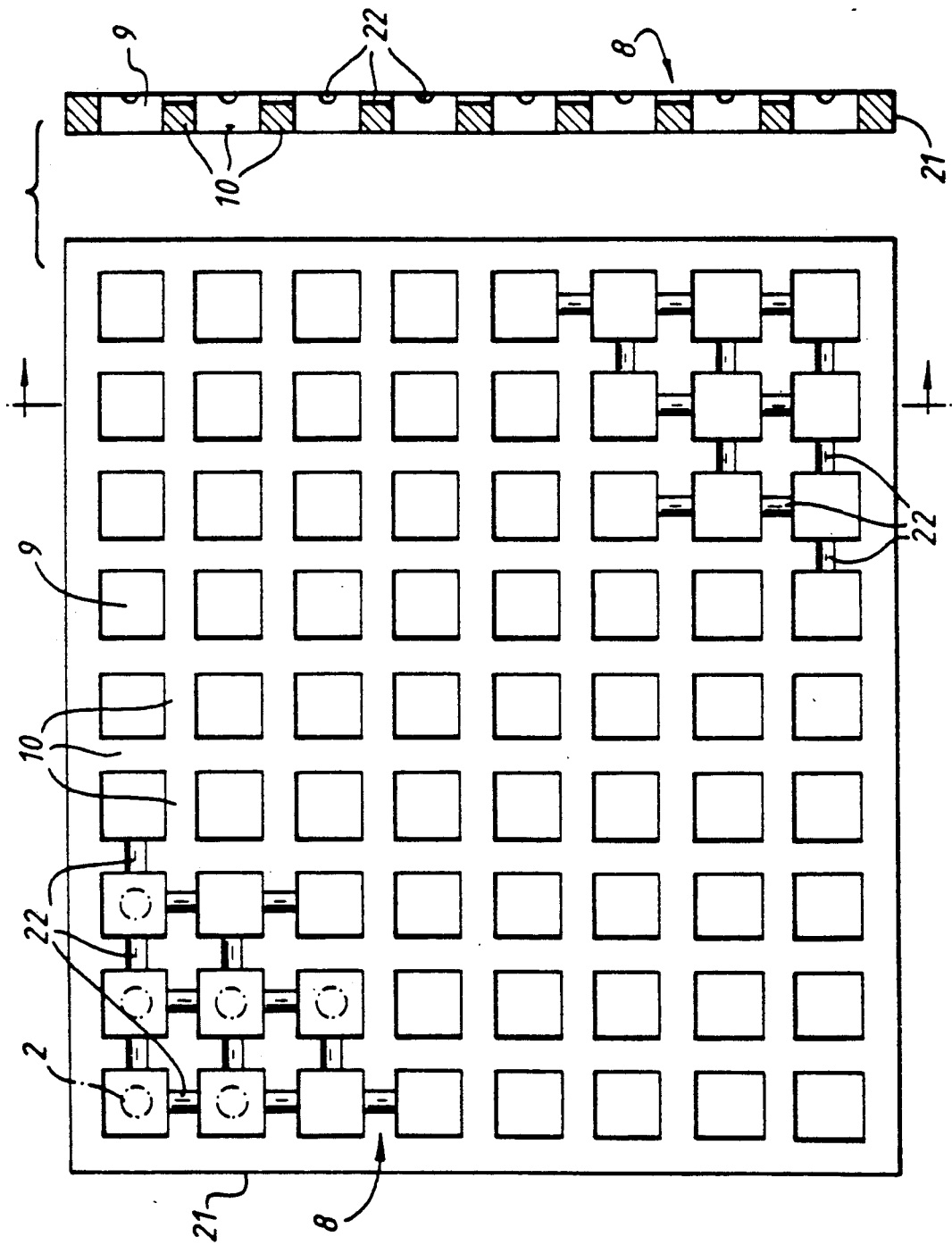
FIG. 2 show plan and side elevational views of part of the structure for defining drift chambers in the detector head assembly of FIG. 1.
Figure 4:
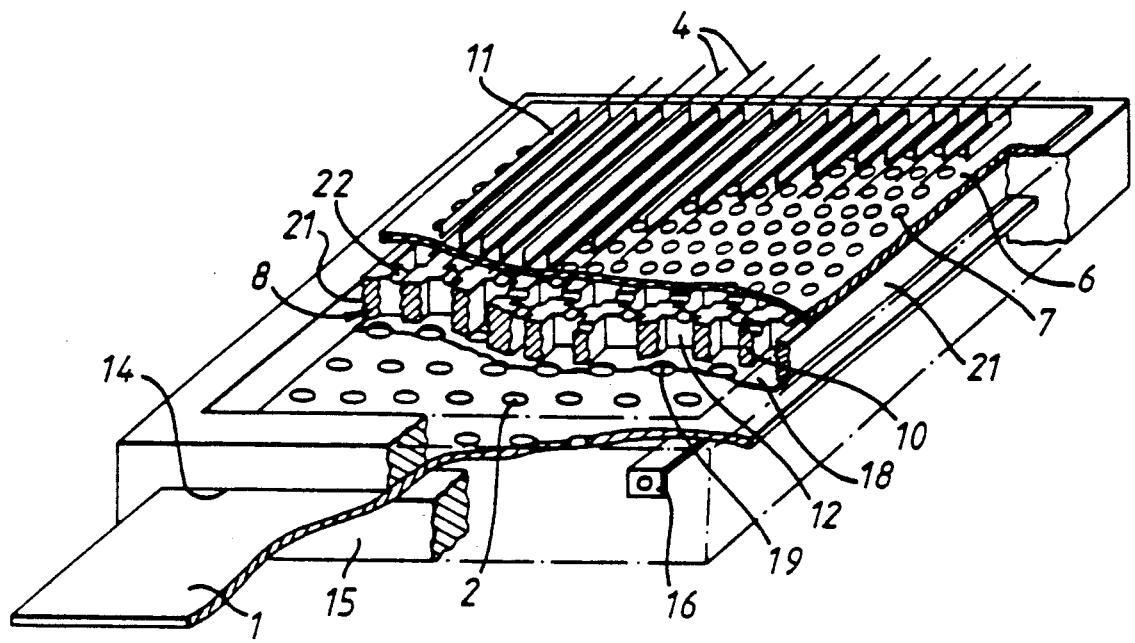
FIG. 4 is a perspective and partly sectional view of the detecting head assembly (in which the grid of cathode strips which cross over the array of anode wires have been omitted for greater clarity).

The sample holder 1 (FIGS. 1 and 4) is capable of holding 72 samples of radio-active material for the simultaneous measurement of beta particle emission. Each sample e.g. a portion of a radiogram or material which is deposited in a very thin layer in one of the sample holders or wells 2 and the sample holder 1 is slidably inserted (like a drawer) in a slot 14 in a frame 15 (FIG. 4). The sample holder 1 is electrically conductive (e.g. it is made of electrically conductive material) and it engages electrically conductive spring contacts 16 as the holder 1 slides into the frame 15. Contacts 16 are connected to a source of negative potential 17 (FIG. 1), which is preferably and typically of the order of −1000V. The apertured plate 8 (FIG. 2), the mask 6 and the walls 11 are also electrically conductive and are grounded or earthed (0V). A sheet or layer of insulating material 18, with through holes 19 corresponding with the respective wells 2 in the sample holder 1, is interposed between the conductive plate 8 and the conductive sample holder 1.

The clearance between he insulating sheet 18 and the slot 14 is sufficient to enable the holder 1 to be slidably inserted and removed whilst maintaining minimum gas leakage (see below). The periphery 21 (FIG. 2) of the apertured plate 8 is firmly secured and sealed to the frame 15 in order to make a gas-tight seal. The mask 6 is supported by the upper surface of the apertured plate 8 (with which it is in electrical contact) and light clamping pressure is applied so as to secure the detecting electrode sub-asssembly and the mask 6 in the correct position (see FIG. 3) and to maintain little or no gas leakage around the side edges of the detecting electrode sub-assembly and the mask 6. Various methods of constructing detecting electrode sub-assemblies are described in EP-A-0112645 and these methods may be adopted or modified to suit the detecting head assembly of the preferred embodiment of the invention. Hence, no further details of the detecting electrode sub-assembly will be given.

The drift chambers 12 are flooded with a continuous stream of gas or mixture of gases (e.g. 90% argon, 10% methane) which is ionized by the radioactivity (beta particle emission) of the samples. A continuous throughput of gas is necessary with an unsealed system. However, a sealed system (e.g. for detecting more energetic particles such as $^{14}C$) could alternatively be contructed, e.g. by employing an insulating sheet 18 made of very thin material or containing windows of thin material (such as Mylar or mica) and by sealing the detecting electrode (sub-assembly and mask 6 to the upper part of the frame. Despite this a construction without windows is preferred because it permits the detection of Tritium ($^3H$) and also facilitates decontamination and interchangeability of components to suit particular requirements.

It will be noticed, in FIG. 4, that slots or recesses 22 are provided in the upper edges of the walls 10 of the apertured plate 8 to allow intercommunication between adjacent drift chambers 12, thereby allowing the gas or gases to permeate through the structure. To simplify the drawings, a casing which would cover the top of the detector head assembly has not been shown, such a casing having an inlet for the gas or gas mixture (the outlet being provided by leakage, e.g. around the edges of the sample holder 1).

Figure 3:
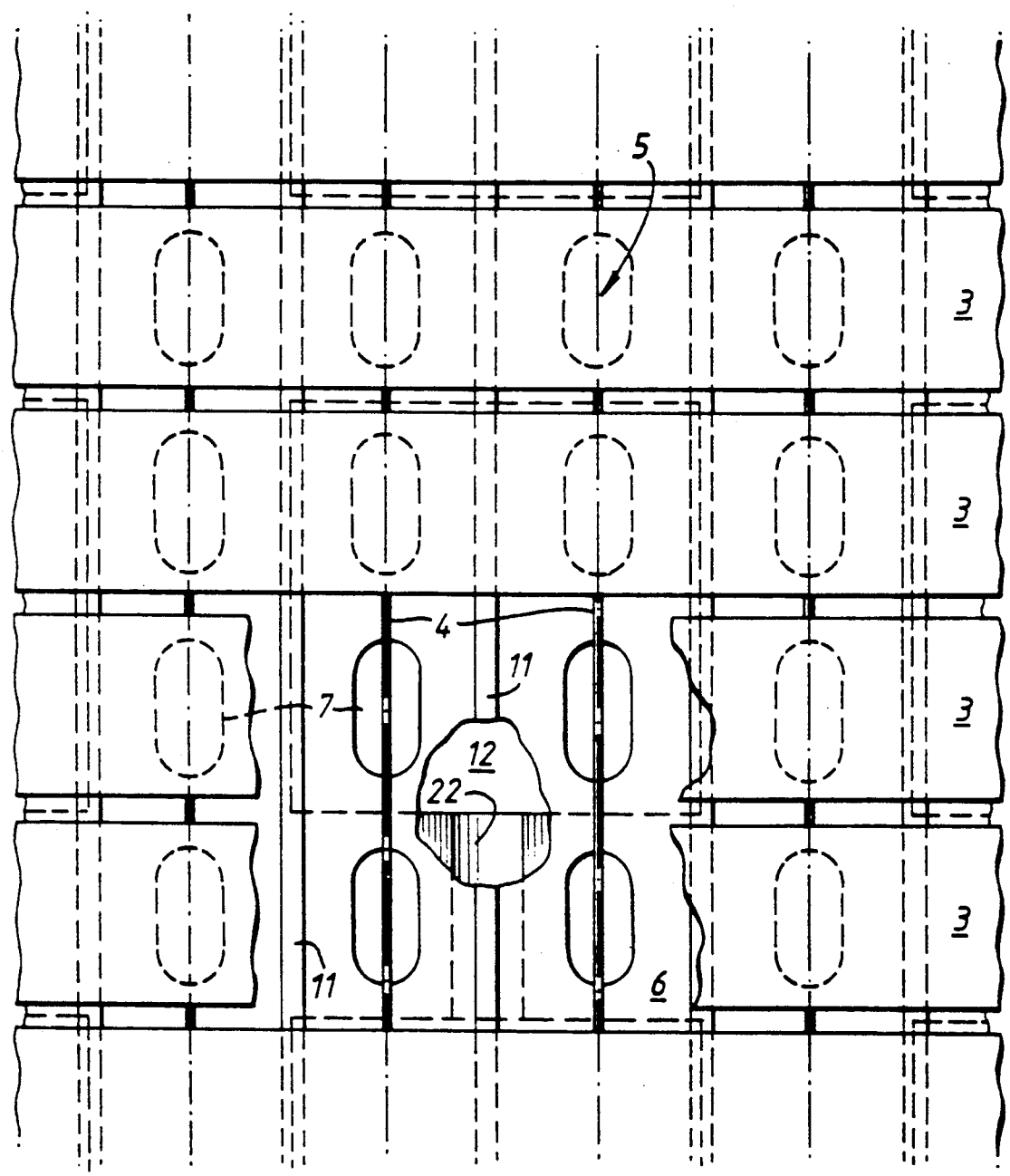
FIG. 3 is a plan view of part of the structure which defines the apertures shown in the structure of FIG. 1.

FIG. 3 is a plan view which shows, in more detail, the relationship between the through holes 7 (in mask 6), the sample receiving zone 2 and the anode/cathode crossing points 5. The plan view is partly cut away to show the underlying structures. As shown in FIG. 3, each sample receiving zone 2 has four mask through holes 7, each hole 7 having its respective anode/cathode crossing point 5. The cathodee electrodes 3 are relatively wide strips which cross-over sections of the anode wires 4, the cross-over being centralised with respect to the geometric center of the respective hole 7 in the mask 6. The space between adjacent cathode strips is preferably kept as small as possible.

In contrast to the detecting head assembly described in EP-A-0112645, no scanning means is necessary with the detecting head assembly of the preferred embodiement of this invention. The latter detector head assembly may thereby be termed a "fixed" head, as opposed to a "scanning head". However, the drift chamber concept could be used with the scanning means and mask of EP-A-0112645 in order to provide high spatial resolution together with high sensitivity.

As seen in FIGS. 1, 3 and 4, the isolating walls 11, which are made of conductive material, are supported by, and in electrical contact with, the upper surface of the conductive mask 6. The apertured plate 8, mask 6 and walls 11 are thereby earthed or grounded (0V), whereas the conductive sample holder 1 is connected to a (preferably variable) source 17 of negative potential, typically of the order of −1000V. This potential difference creates an electric field within each of the drift chambers 12, the field being directed so as to cause negative ions to drift towards the mask 6 and to pass through the holes 7 and be captured by the anode wires 4. The isolating walls 11 serve to reduce mutal interference between adjacent anode wires 4 hence preventing any "cross-talk".

Figure 5:
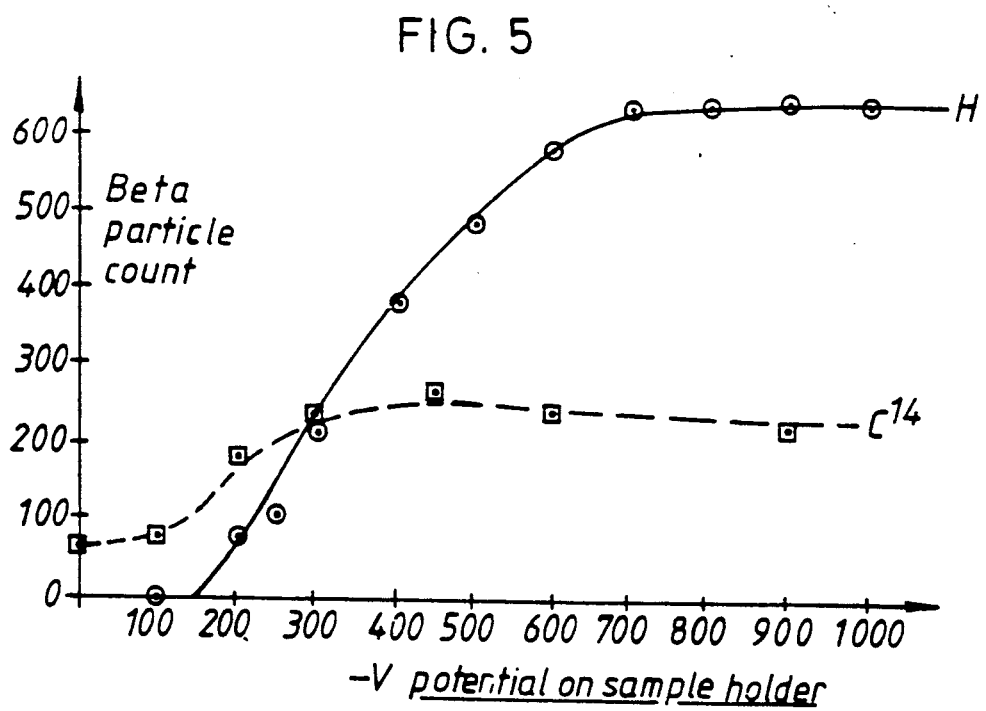
FIG. 5. is a graph showing the effect on beta particle count of increasing the potential difference which creates the field within the drift chambers.

The application of the electric field has the effect of increasing the efficiency of collection of the negative ions due to beta particle emission from a given radioactive sample. FIG. 6a and 6b schematically illustrate the effect of the electric field. Beta particles are emitted from the sample in all directions over a $2\pi$ steradian solid angle. In the absence of the field, a high proportion of ions due to these particles collide with the mask 6 and the walls 10, or recombine and are lost. However, in the presence of the field a significant proportion of these ions is "funnelled" into the hole 7 in mask 6. This increases the detection gain or sensitivity of the system, because more ionizing events are detected than would otherwise be the case without the electric field. The effect is more noticeable as the potential on source 17 is made more negative in order to increase the applied potential difference. FIG. 5 is a graph which illustrates the effect of varying negative potential (i.e. becoming more negative) on beta particle count. In the case of tritium, the count started to increase quite rapidly after exceeding −150 V and reached a maximum with the application of −700 V. With a radioactive carbon sample ($^{14}C$), the beta particle count started to increase with the application of a negative potential in excess of −100 V and reached a maximum for a negative potential of about −450 V. Clearly, the optimum negative potential will depend on the purpose for which the detector head assembly is used and on its particular geometry.

The effect described above is surprising in that no specially designed focussing structures (e.g. of conventional form) were used to funnel the negative ions through the apertures 7 in the mask 6. Hence, a worthwhile increase in sensitivity was gained, but not at the expense of a complicated structure.

The anode wires 4 are preferably connected to conventional signal processing means, such as the type which employ delay lines as mentioned above, in order to produce signals related to position coordinated (i.e. coded signals). However the wires 4 may alternatively be connected to coding devices which supplies binary coded signals to a computer as described in EP-A-0112645.

In the case of the detecting head according to the preferred embodiment of the invention, the samples may be a dried down solution or a portion or portions of one or more radiograms (e.g. each sample may be a portion of a different radiogram), each portion being placed in one of the sample receiving zones or wells 2.

As mentioned above, each sample receiving zone has four apertures with corresponding anode/cathode crossing points 5. The computer will therefore process data relating to coded signals representing the respective counts at each of these four locations for each of the samples. For example, the coded signals at each of these four locations are totalised to provide a total beta particle count for the respective sample. These counts are then either displayed, or printed out (or both), as a row by column matrix corresponding with the 72 positions in the sample holder 1.

There is only a low probability of coincidence of individual ionizing events which might be detected by the same anode wire 4 or cathode strip, i.e. the anode wire 4 or cathode strip 3 which is shared by adjacent drift chambers. Hence, the coded signals (coded with regard to a row by column matrix) generally represent the occurrence of ionization events at the respective sample positions since coincidence of such events on the same anode wire is a minor factor. Such coincidences as may occur do so at random positions and only contribute uniformly to the background in a predictable way.

Whilst the above description refers to the counting of beta particles, the detecting head assembly may also be used (with suitable modification) to detect alpha particles. Moreover, the detecting head assembly can be used for counting radioactive emissions from any sample which can be contained by a well 2 (and which is as thin as possible to reduce self absorption of radiation) as long as it is capable of ionizing a gas within the chamber 12.

The principal advantages of the detecting head assembly described above are that (a) substantially all of the radioactivity emitted from one side of a sample is detected and hence the assembly has greater sensitivity than conventional detectors placed over but at a distance from samples, (b) detection is sensibly independent of sample position in the wells 2 of holder 1, i.e. small changes in sample position give rise to negligible change in sensitivity, and (c) detection of the radioactivity from any given sample is sensibly independent of the distribution of that radioactivity in the sample, i.e. in one of the wells 2.

The detecting head assembly described above is not confined to the use of "dry" samples since the sample receiving zones 2 in each column (or row) of the sample holder 1 could be replaced by shallow grooves each covered by a radiation transmissive window and each provided for receiving a liquid or gas which carries eluted components of a substance to be measured. For example, the substance may be separated into components by means of electrophoresis, or chromatography. The separated components are then carried in the fluid which is caused to flow through the sample grooves. A thin radiation transmissive window over each groove (such as a sheet of Mylar about 5 microns thick) allows radiation (such as beta particles) to pass through whilst preventing contamination of the detector head assembly, e.g. due to liquid spillage or leakage of radioactive gas. As the fluid passes through the grooves, ionization takes place in the corresponding drift chambers 12 (due to the radioactive components) and the count (derived from the respective crossing points 5) represents the distribution of radioactivity along the length of a particular groove with respect to time. Hence, besides measuring radioactivity in a number of samples simultaneously, it is also possible to measure the temporal distribution of radioactive components and this adds a further dimension to the analysis of a sample.

Whilst the fluid carrying the eluted components (from either electrophoresis, or chromatography) may be caused to flow continuously through the groove, the fluid flow may be varied, or stopped and restarted, and/or the conditions of separation may be varied or separation stopped, at different times, so as to achieve the effect required. For example, fluid may flow into a groove and the flow stopped when certain radioactive components have travelled a certain distance into the groove or when there is a particular pattern of activity in a number of grooves. Counting may then be carried out for a suitable period before the flow is restarted, or the groove may be flushed out before another sample is taken.

The modified sample holder described above (for use with liquids or gases, could also be used with conventional or other detecting head assemblies to measure both spatial and temporal radioactivity distributions (i.e. assemblies other than defined in the appended claims).

The assembly described above is but one example of how the invention may be employed in practice and various other modifications and changes may be made to suit individual requirements without departing from the scope of the claimed invention.

I claim:

1. A detector head assembly capable of simultaneously detecting radioactive emissions from a multiplicity of samples, said assembly comprising:
   (a) a sample holder which defines a multiplicity of sample receiving zones;
   (b) a structure defining a multiplicity of drift chambers corresponding respectively with said sample receiving zones, the structure defining each of said drift chambers having one or more apertures for passage therethrough of ions resulting from ionization of gas within said chambers due to radioactive emission;
   (c) detecting electrode means including an array of anodes which are disposed transversely to an array of cathodes so as to define therewith a plurality of crossing points, said crossing points being disposed so as to correspond with the respective apertures in said structure; and
   (d) means for isolating neighbouring regions in the vicinity of said crossing points so as to reduce, or substantially eliminate mutual interference between adjacent crossing points;
   the arrangement being such that a potential difference can be applied across the sample holder and said structure to create a field within each of said drift chambers, which field causes said ions to pass through said apertures for detection by the respective crossing points, said field being applied to improve the detection gain of the detector head assembly.

2. An assembly according to claim 1, wherein the structure defining the drift chambers includes a first plate containing the apertures and a second apertured plate defining walls of the drift chamber which extend between the first plate and the sample holder.

3. An assembly according to claim 2 wherein said second plate is of integrally moulded form.

4. An assembly according to claim 3, wherein said second plate is made of electrically conductive material.

5. An assembly according to claim 1 wherein said structure is such as to define drift chambers of substantially square cross section.

6. An assembly according to claim 1, wherein said isolating means comprises walls defining channels in which the anode electrodes are located.

7. An assembly according to claim 1, wherein said sample holder is made of electrically conductive material.

8. An assembly according to claim 7, wherein said sample holder is insulated from said structure by a sheet or layer of insulating material having radiation transmissive zones or apertures therein corresponding with the respective sample receiving zones.

9. An assembly according to claim 1, wherein said sample holder is slidably received within the detector head assembly.

10. An assembly according to claim 1 and further including means to introduce a gas or mixture of gases for the purpose of ionization, said gas or gas mixture being continuously supplied, in use, to the assembly and escaping therefrom by minimum leakage.

11. An assembly according to claim 10, wherein said structure includes passageways to allow intercommunication between adjacent drift chambers for said gas or gas mixture.

* * * * *